United States Patent [19]

Hall

[11] Patent Number: 5,046,199
[45] Date of Patent: Sep. 10, 1991

[54] GOGGLES

[75] Inventor: Stephen J. Hall, Langley, Canada

[73] Assignee: S. Acquisition Corp., Van Nuys, Calif.

[21] Appl. No.: 557,118

[22] Filed: Jul. 23, 1990

[51] Int. Cl.$^5$ .............................................. A61F 9/02
[52] U.S. Cl. ......................................... 2/446; 2/445; 2/452
[58] Field of Search ................... 2/426, 431, 440, 442, 2/443, 444, 445, 446, 452, 454

[56] References Cited

U.S. PATENT DOCUMENTS

| D. 237,757 | 11/1975 | Turner . | |
|---|---|---|---|
| 1,369,040 | 2/1921 | Malcom | 2/445 |
| 2,007,186 | 7/1935 | Farrell | 2/14 |
| 2,103,575 | 12/1937 | Diggins | 88/41 |
| 2,139,811 | 12/1938 | Dockson et al. | 2/14 |
| 2,290,938 | 7/1942 | Bouchard | 2/14 |
| 2,709,256 | 5/1955 | Baratelli | 2/14 |
| 3,147,489 | 9/1964 | Nelson | 2/14 |
| 3,605,116 | 9/1971 | Simpson et al. | 2/14 |
| 4,264,987 | 5/1981 | Runckel | 2/428 |
| 4,348,775 | 9/1982 | Haslbeck | 2/452 |
| 4,468,819 | 9/1984 | Ohno | 2/430 |
| 4,564,960 | 1/1986 | Nishiyama | 2/452 |

FOREIGN PATENT DOCUMENTS

| 1004403 | 2/1977 | Canada | 2/440 |
|---|---|---|---|
| 2052245 | 1/1981 | United Kingdom | 2/440 |

Primary Examiner—Werner H. Schroeder
Assistant Examiner—Michael A. Neas
Attorney, Agent, or Firm—Amster, Rothstein & Ebenstein

[57] ABSTRACT

Goggles include a pair of eyepieces, an elongate nosepiece connecting the pair of eyepieces to form an assembly, and a fastener securing the assembly on a wearer's head. The nosepiece has a flexible bridgepiece adapted to pass over the bridge of the wearer's nose and, at each end of the bridgepiece, an end ring defining an aperture. Each of the eyepieces is rigid and defines a lug extending inwardly towards the bridgepiece and a pin disposed rearwardly of the lug and extending inwardly. The lug defines a passageway therethrough for a respective one of the end rings, and the pin is configured and dimensioned to enter and engage the aperture of the respective one end ring. The pin and lug cooperatively preclude accidental disengagement of the end ring aperture and pin, whereby the nosepiece and eyepieces are releasably locked together to form the assembly.

19 Claims, 4 Drawing Sheets

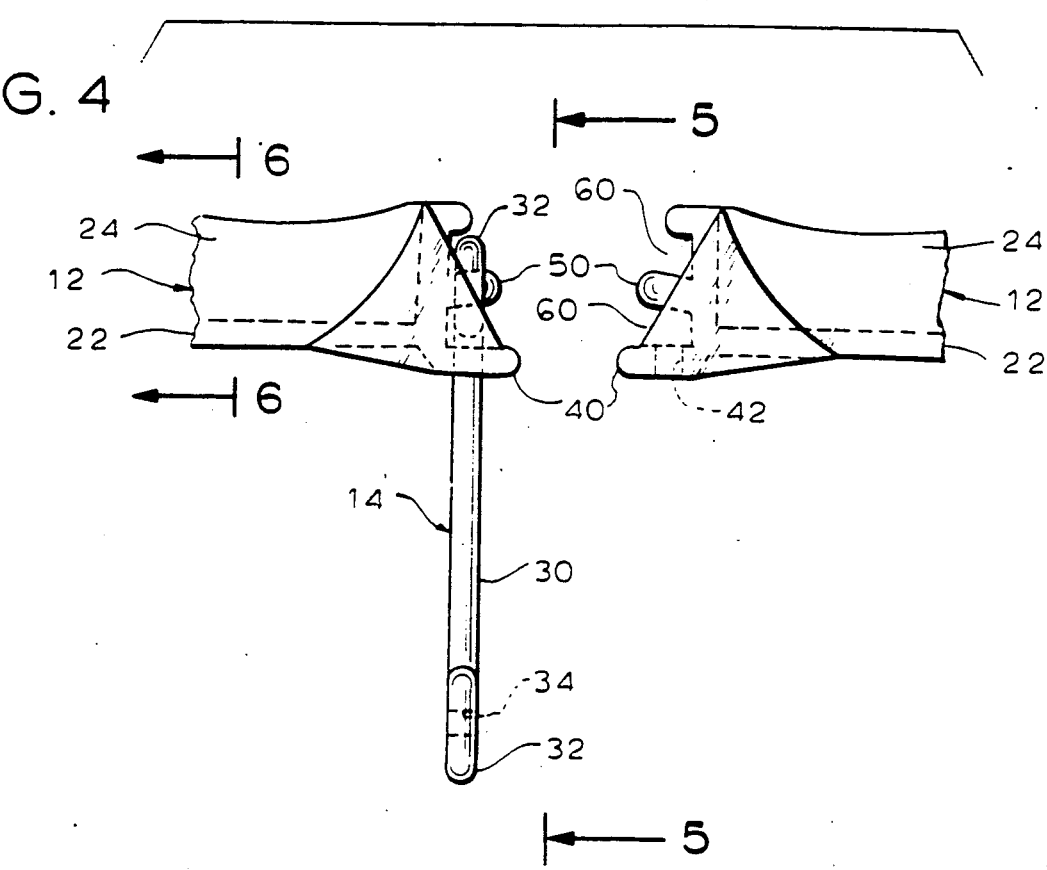
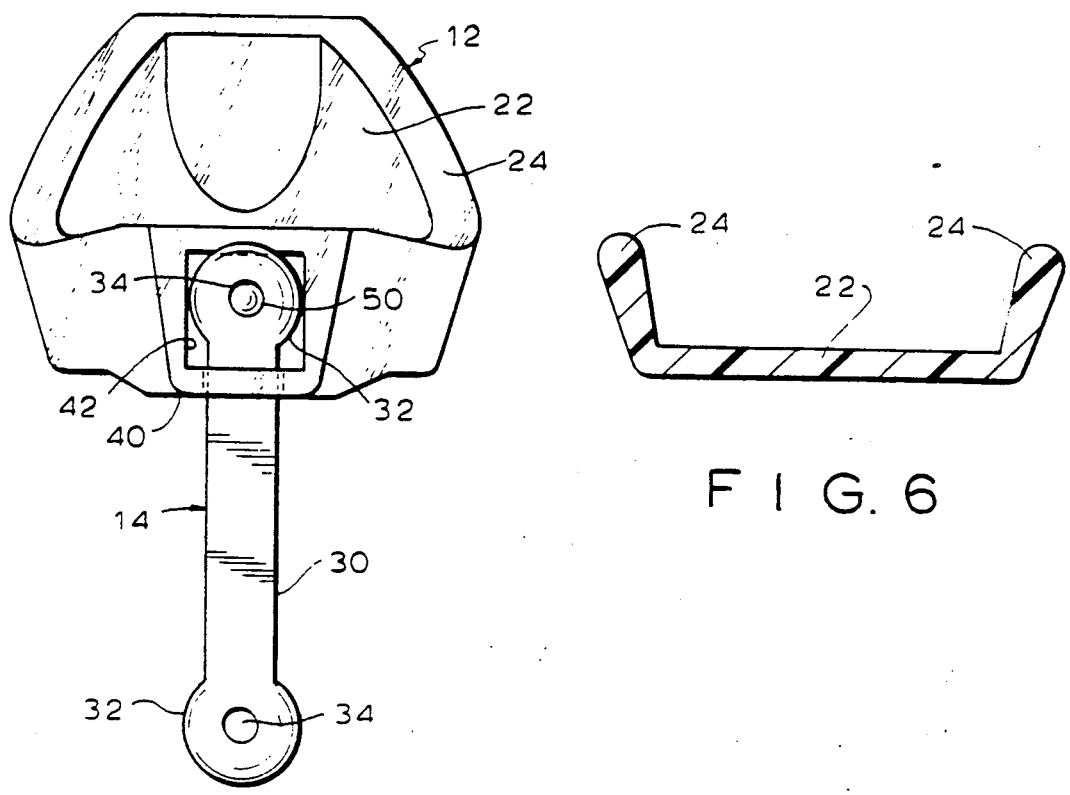

GOGGLES

BACKGROUND OF THE INVENTION

The present invention relates to goggles and more particularly to goggles having a flexible nosepiece which connects the two eyepieces.

While there are a variety of goggles having a flexible nosepiece which connects two eyepieces, typically the engagement between the nosepiece ends and the eyepieces are not locked. Accordingly, during use of the goggles, one or both of the eyepieces may accidentally become separated from the nosepiece, thereby permitting the goggles to fall away from the wearer's face and, indeed, become lost. Alternatively, again because the engagement between the eyepieces and the nosepiece are not locked, one or both of the eyepieces may move closer to the other along the nosepiece (especially during storage of the goggles), with the result that the effective length of the nosepiece is shortened and the goggles must be readjusted prior to wearing. Finally, in such goggles, the engagements between the nosepiece and the eyepieces may depend upon an irregular contouring of the nosepiece profile—for example, a profile defining a series of grooves adapted to engaged an eyepiece. Such a contour may not be comfortable on the wearer's nose if on the inner surface and/or may be unattractive in appearance if on the outer surface. Further, such contouring may reduce the flexibility of the nosepiece such that the mating of the rear of the eyepieces and the front of the wearer's face is unreliable and cushioning must be provided on the periphery of the eyepiece backs to insure an intimate contact which excludes deleterious particles and fluids in the environment from reaching the wearer's eyes. The proper positioning and securing of such cushioning on the rear of the eyepieces is, however, an expensive and arduous procedure, increasing the overall cost of the goggle.

U.S. Pat. No. 2,290,938 discloses goggles having a flexible nosepiece in the form of a strap member connecting a pair of eyepieces or eye cups. The nasal or inner side of each eyepiece has a first slot, a notch, and a second slot in an overhanging nasal wall, and each end of the flexible strap must be threaded in turn through the first slot, the notch, the second slot and finally the first slot again. A slotted buckle is used to connect the free ends of the flexible strap, and the free ends must therefore be appropriately threaded through the slots of the slotted buckle in order to lock the eyepieces together by the flexible strap.

Clearly, in such goggles the eyepieces and the slotted buckle must be made with considerable precision to provide the necessary slots and notches therein, and the assembly of the eyepieces and nosepiece is an elaborate, lengthy and labor-intensive procedure, all of which must be reflected in the cost of the goggles. The presence of the relatively rigid slotted buckle on the bridgepiece may be uncomfortable to the bridge of the wearer.s nose, and, if the wearer falls or is impacted about the bridge of his nose, the slotted buckle may cause injury. Nonetheless, such goggles having a flexible nosepiece are preferred to goggles having a rigid nosepiece because the flexibility of the nosepiece enables it and the eyepieces to more closely conform to the face of the wearer, thereby avoiding a need for the equally arduous and costly placement of cushioning on the rear of the eyepieces (adapted to contact the face of the wearer) in order to seal the eyepieces to the wearer's face and thus protect the wearer's eyes from the environment. Thus, a need remains for goggles which are easily and inexpensively manufactured and assembled.

Accordingly, it is an object of the present invention to provide goggles having a pair of eyepieces connected by a flexible nosepiece, said goggles being easy and inexpensive to manufacture and assemble.

Another object is to provide such goggles in which the nosepiece does not require a slotted buckle to connect the end pieces thereof.

A further object is to provide such goggles in which the eyepieces do not require cushioning on the rear thereof.

SUMMARY OF THE INVENTION

The above and related objects of the present invention are obtained in goggles comprising a pair of eyepieces, an elongate nosepiece connecting the pair of eyepieces to form an assembly, and means for securing the assembly on a wearer's head. According to the present invention, the conventional goggles are improved by providing the nosepiece with a flexible bridgepiece adapted to pass over the bridge of the wearer's nose and, at each end of the bridgepiece, an end ring defining an aperture. Each of the eyepieces is rigid and defines a lug extending inwardly towards the bridgepiece and a pin disposed rearwardly of the lug and extending inwardly. The lug defines a passageway therethrough for a respective one of the end rings, and the pin is configured and dimensioned to enter and engage the aperture of the respective one end ring. The pin and the lug cooperatively preclude accidental disengagement of the end ring aperture and the pin, whereby the nosepiece and the eyepieces are releasably locked together to form the assembly.

Preferably, the goggles are sports goggles, such as swim goggles, and are characterized by the absence of cushioning on the rear of the eyepieces. The means for securing the assembly on a wearer's head may comprise an elastic band which, in conjunction with the pair of eyepieces and the nosepiece, encircles the wearer's head.

In a preferred embodiment, each of the end rings is flexible and resilient. The lug passageway has a dimension less than that of the end ring, so that the end ring must be compressed in that dimension for passage through the lug passageway. The free end of the pin is tilted rearwardly away from the lug, whereby the respective one end ring is locked onto the pin while a force in the forward direction is applied to the respective one end ring. The pin extends inwardly towards the bridgepiece at least as far as the lug passageway and is spaced rearwardly of the lug a distance sufficient to enable the passage therebetween of the respective one end ring. The nosepiece is resilient and preferably formed of an elastomeric material such as rubber.

In another preferred embodiment, the goggles include a pair of eyepieces and an elongated nosepiece for connecting the eyepieces, the improvement comprising the nosepiece being fabricated of an elastomer and including integral female attachment members at opposite ends thereof. Each of the eyepieces includes at the inner side thereof an integral male member releasably receiving and engaging the adjacent female member, the corresponding engaged male and female members being oriented relative to each other such that the force normally exerted thereon by the nosepiece is in a direction to preclude inadvertent disengagement.

Preferably, the goggles include guide means formed on each of the eyepieces and positioned in relation to the male member to engage the contiguous end of the nosepiece and orient the same for attachment of the female member to the male member. The guide means may simply be a slot formed in the eyepiece having its major axis at an obtuse angle to the major axis of the male member, the female member preferably being compressible in at least one dimension to enable it to pass through the slot. The male and female members are configured to snuggly engage.

The present invention further includes a method of assembling the goggles by inserting each end ring through the passageway defined by a respective lug and then engaging the pin in the aperture of the end ring. The securing means is applied to the outer end of each eyepiece.

In a preferred embodiment, each of the end rings is flexible and resilient, and each of the lug passageways has a width and/or height less than that of the end ring, with the method including the step of compressing the end ring in width and/or height for insertion through the lug passageway.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein:

FIG. 4 is a fraqmentary side elevational view of the goggles, with the nosepiece being assembled with one of the eyepieces, but not the other;

FIG. 5 is a sectional view thereof, taken along the line 5—5 of FIG. 4; and

FIG. 6 is a sectional view of the eyepiece, taken along the line 6—6 of FIG. 4.

DETAILED DESCRIPTION OF THE PREFERRED EMBODIMENTS

Figure 1:
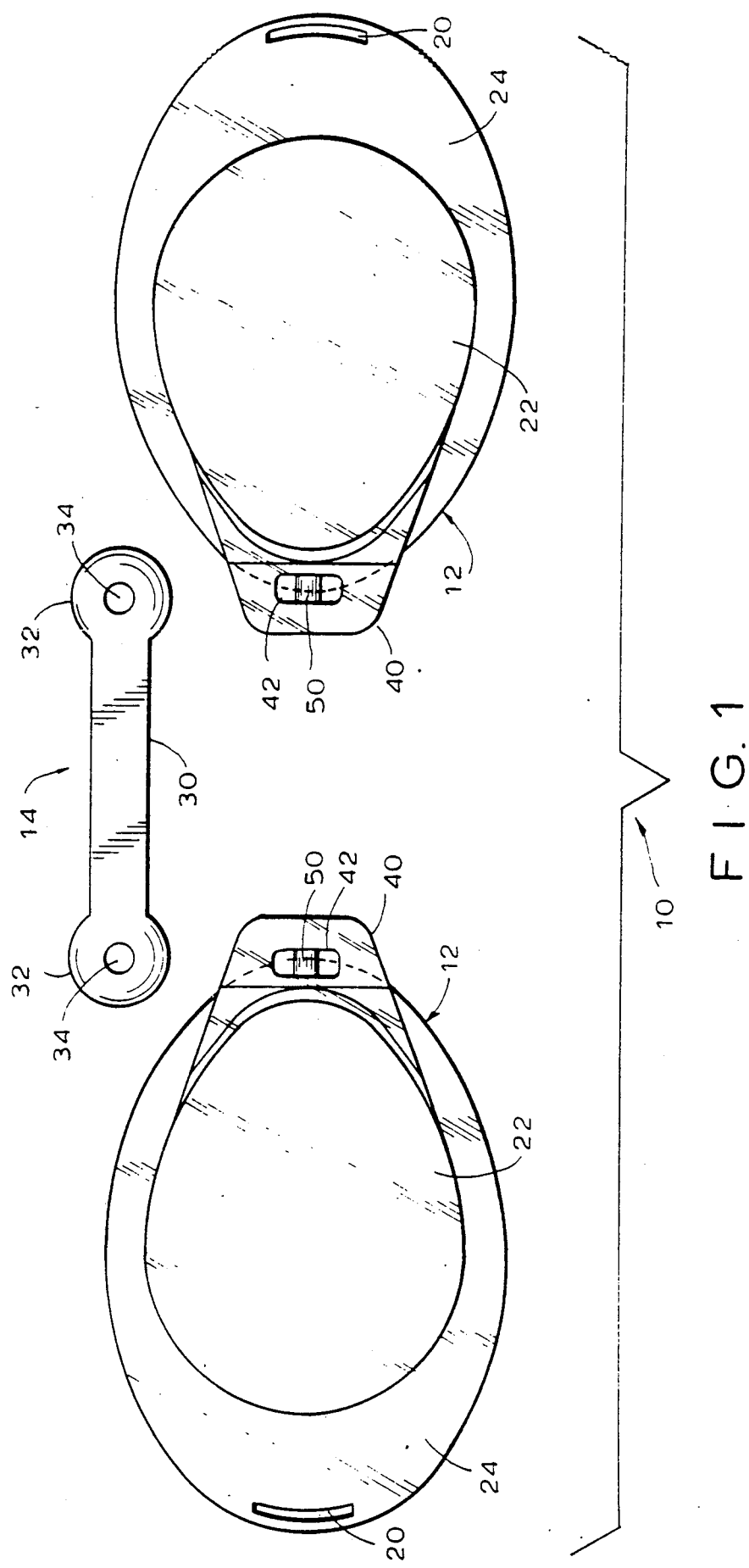
FIG. 1 is an exploded front view of goggles according to the present invention without the securing means.
Figure 2:
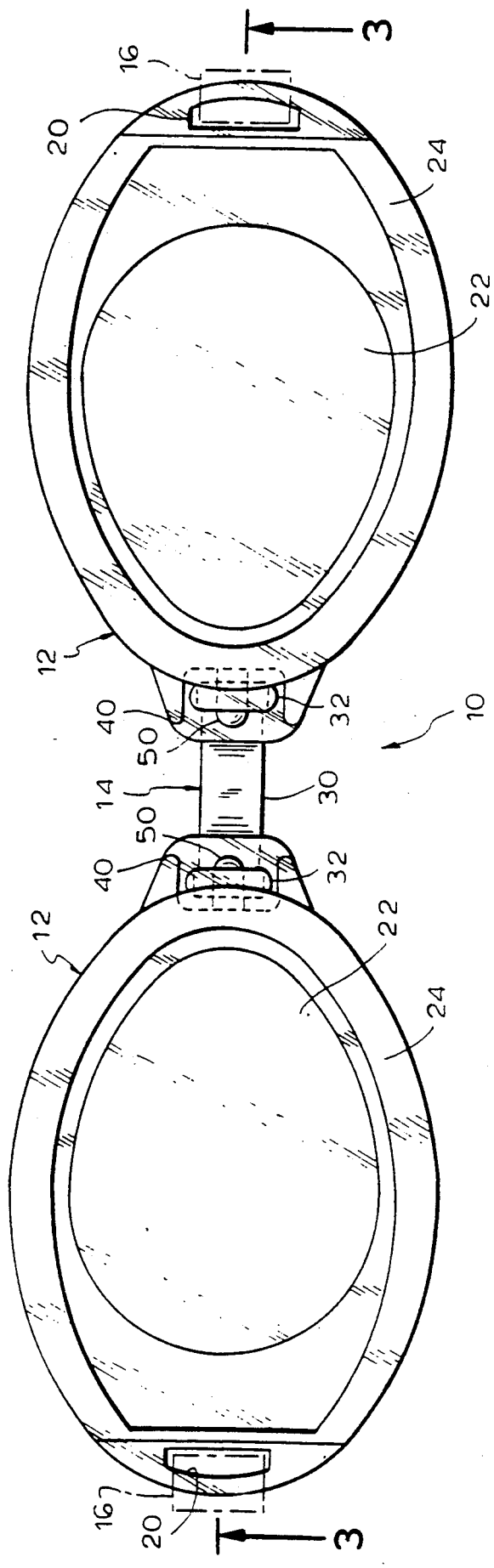
FIG. 2 is a rear assembly view thereof, with the securing means shown in phantom line; line 3—3 of FIG. 2, with the securing means shown in phantom line.
Figure 3:
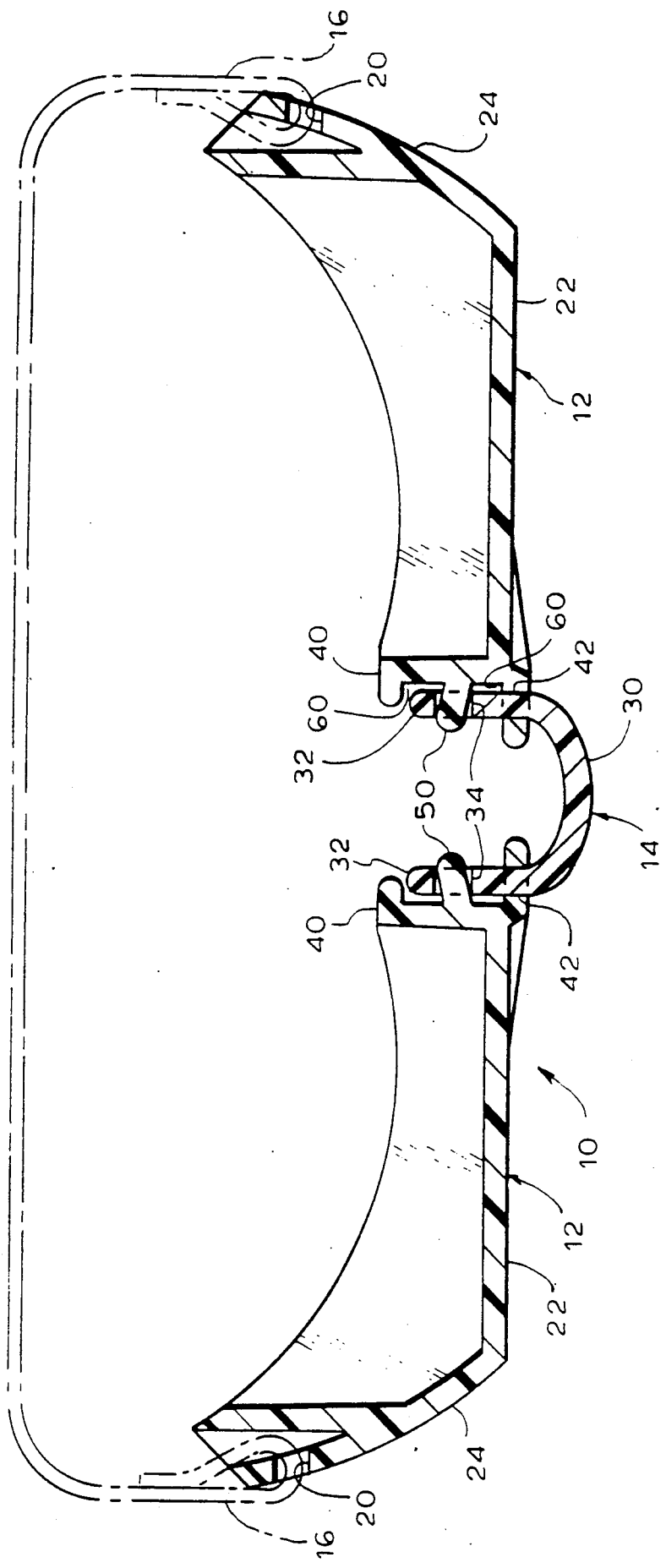

Referring now to the drawing, and in particular to FIGS. 1-3 thereof, therein illustrated are goggles generally designated by the reference numeral 10. While the goggles 10 are preferably sports goggles, and in particular swim or underwater goggles, the goggles may also be safety goggles (with unbreakable lenses), decorative goggles, or the like, without departing from the principles of the present invention as set forth hereinbelow. In its conventional aspects, the goggles 10 comprise a pair of eyepieces generally designated 12, an elongate nosepiece generally designated 14, and securing means generally designated 16 (not shown in FIG. 1 and shown in phantom line in FIGS. 2 and 3) for securing the assembly of the eyepieces 12 and nosepiece 14 on a wearer's head (not shown).

Preferably each of the eyepieces 12 is integrally molded of rigid plastic (or formed of other suitable material) and is of unitary, one-piece, integral construction. Alternatively, the eyepieces 12 may simply be eye cups adapted to receive glass or plastic lenses 22 therein. The rigid lens 22 of each eyepiece 12 is surrounded by a rigid rim or eye cup 24 adapted to engage the wearer's head about an eye socket and appropriately position the lens 22 while spacing it forwardly of the wearer's eye. The outer lateral portion of each eyepiece 12 defines a slot 20 through which passes means 16 for securing the assembly of the nosepiece 14 and the eyepieces 12 on the wearer's head. While the securing means 16 is illustrated as an elastic strap in FIGS. 2 and 3 (in phantom line), a variety of other means may be used, including adjustable non-elastic straps, temple pieces (whether hingedly connected to the eyepieces 12 or not), etc., and means other than slots 20 may be used to connect the securing means 16 to the eyepieces 12. As the goggles 10 discussed herein above are conventional in nature and well-known to those familiar with the goggles art, further details thereof need not be set forth herein.

In its novel aspects, the goggles 10 of the present invention comprise a nosepiece 14 having a flexible and resilient bridgepiece 30 adapted to pass over the bridge of the wearer's nose and, at each end of the bridgepiece 30, an end ring 32 defining a small central aperture 34. While the dimensions of the nosepiece 14 will, of course, vary with the dimensions of the intended user, a preferred nosepiece 14 for swim goggles has a thickness of about 0.125 in., a width at the bridgepiece 30 of about 0.22 in., a width at each end ring 32 of about 0.35 in., and a diameter for each small central aperture 34 of about 0.100 in. While these dimensions are generally suitable for all goggles, clearly they may be varied within reason as necessary in order to meet particular desired applications. The dimension which is more likely to vary with the size of the user is the centerpoint-to-centerpoint spacing between the small holes 34, such spacing ranging from about 1.045 in. to about 1.220 in.

The in ner or medial aspect of each eyepiece 12, and in particular the rim 24 thereof, defines a medially projecting lug 40 extending inwardly or medially towards the bridgepiece 30 of the nosepiece 14. The lug 40 defines a slot or passageway 42 therethrough adapted to enable passage therethrough of a respective one of the end rings 32. A preferred passageway 42 for the preferred end ring 32 described above has a height of about 0.125 in. and a width of about 0.260 in. As the end ring 32 is to be passed from the front of the passageway 42 through the rear thereof, the end ring 32 must be compressed in at least one dimension—namely, width (from 0.35 in. to 0.260 in.)—for its passage through the passageway 42.

The inner or medial aspect of each eyepiece 12, and particular the rim 24 thereof, additionally defines a pin 50 disposed rearwardly of the lug 40 and extending inwardly or medially towards the bridgepiece 30. The pin 50 is configured and dimensioned to enter and engage the small central aperture 34 of an end ring 32 once the end ring 32 has passed through the passageway 42 and resumed its uncompressed or natural dimensions. Thus a preferred pin 50 for use with the preferred end ring 32 described above has a diameter of about 0.100 in., the same as the end ring central aperture 34. The free end of the pin 50 is tilted rearwardly away from the lug 40 (and towards the wearer's face) sc that an end ring 32, which is disposed on a pin 50 (which enters and engages its small central aperture 34), is locked onto the pin 50 by a force in the forward direction applied to that end ring 32.

The tilt of the pin 50, and in particular the obtuse angular disposition of the major axis of pin 50 relative to the major axis of lug passageway 42 (i.e., the axis along which the end ring 32 passes), insures that the forces applied by the nose of the wearer on the nosepiece 14 are translated into a forward and lateral force on the end ring 32, such force acting to maintain and releasably lock the engagement of the pin 50 and the end ring 32. Typically, a slight rearward angling of the free end of pin 50 is sufficient for this function, a rearward angle of about 10 degrees being preferred. The pin 50 preferably extends medially (that is, inwardly towards the bridgepiece 30) at least as far as the innermost extent of the lug passageway 42. Thus the constrained path of the nosepiece 14 through the passageway 42 prior to its engagement with the pin 50 serves to maintain the force applied to the end ring 32 during normal wear of the goggles 10 forwardly (towards the lug 40) and laterally (away from the nosepiece 30). The resultant camming action exerted by the rearwardly tilted pin 50 acts to maintain engagement of the pin 50 and end ring 32.

In order to facilitate assembly of the nosepiece 14 and eyepiece 12, adequate space 60 must be left around the pin 50, and in particular between the front of pin 50 and the rear of lug 40, so that the annulus of the end ring 32 (preferably about 0.125 in. in width) can be received therein, with the end ring 32 passing onto the base of the pin 50. It will be appreciated that the pin 50 and the lug 40 cooperatively preclude accidental disengagement of the end ring 32 and the pin 50 so that the nosepiece 14 and eyepieces 12 are releasably locked together to form the assembly of the nosepiece 14 and the eyepieces 12.

The nosepiece 14 is preferably formed of an elastomeric material, such as natural or synthetic rubber, which is resilient, flexible and of suitably high tensile strength. A preferred material is Synprene available from Rochevert Company. The rim 24, including the lug 40 and pin 50, is preferably formed of a relatively rigid material such as polycarbonate. The great flexibility, and thus conformability, of the nosepiece substantially eliminates the need for cushioning on the rear of the eyepieces.

Referring now to FIGS. 4-5 as well, in order to form the assembly, an end ring 32 of the nosepiece 14 is inserted rearwardly through a respective passageway 42 of a lug 40 of an eyepiece 12, the end ring 32 being compressed in width suitably for snug passage through the narrower and shorter passageway 42. As the end ring 32 emerges into the space 60, intermediate the lug 40 and the pin 50, it is moved first medially and rearwardly and then laterally and slightly forwardly over the pin 50, thereby causing the pin 50 to enter the small central aperture 34 of the end ring 32 and be snugly maintained thereon. If and when it is desired to separate the eyepieces 12 and the nosepiece 14, the forward and lateral force acting on the end ring 32 is reduced (for example, by feeding more of the bridgepiece 30 through the lug passageway 42), and then the end ring 32 is forcibly lifted off the pin 50 by a rearward and medial motion. Once the end ring 32 is released from the pin 50, it may be pulled through the passageway 42, preferably with manual compression of the end ring 32 in width to facilitate the passage.

One end of securing means 16 is applied in conventional fashion to the lateral aspect of each eyepiece 12, for example, by passage through the slot 20.

It will be appreciated by those skilled in the art that the end rings 32 and pins 50 are merely representative of the female and male members, respectively, which may be used to effect the desired engagement of each eyepiece with its respective nosepiece end. Accordingly, the term "end ring" is used to designate a female member which defines an aperture therein, regardless of the shape of the aperture (e.g., whether it be round or otherwise), and not to suggest the peripheral or external configuration of the member (which may be circular, Polygonal or of other configuration). Similarly, the term "pin" is used to designate a male member which extends outwardly to enter into an aperture of a female member, regardless of the shape of the male member (which may even be curved). The critical aspect of the present invention is that the male and female members are oriented relative to each other in the final goggle assembly such that the force normally exerted thereon by the nosepiece is in a direction to preclude inadvertent disengagement. To that end, the goggles preferably include guide means formed on each of the eyepieces and positioned in relation to the male members to engage the contiguous end of the nosepiece and orient the same for attachment of the female member to the male member. The guide means is preferably a slot or passageway formed in the eyepiece having its major axis at an obtuse angle to the major axis of the male member.

To summarize, the present invention provides goggles having a pair of eyepieces connected by flexible a nosepiece, the goggles being easy and inexpensive to manufacture and assemble. Further, the goggles do not require a slotted buckle to connect the end pieces of the nosepiece or cushioning on the rear of the eyepieces.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing disclosure.

I claim:

1. In goggles comprising:
   (A) a pair of eyepieces;
   (B) an elongate nosepiece connecting said pair of eyepieces to form an assembly; and
   (C) means for securing said assembly on a wearer's head;
   the improvement wherein:
   (i) said nosepiece has a flexible bridgepiece adapted to pass over the bridge of the wearer's nose and, at each end of the bridgepiece, an end ring defining an aperture, and
   (ii) each of said eyepieces is rigid and defines a lug extending inwardly towards said bridgepiece and a pin disposed rearwardly of said lug and extending inwardly, said lug defining a passageway therethrough for a respective one of said end rings, and said pin being configured and dimensioned to enter and engage said aperture of said respective one end ring, said pin and said lug cooperatively precluding accidental disengagement of said end ring aperture and said pin, whereby said nosepiece and said eyepieces are releasably locked together to form said assembly.

2. The goggles of claim 1 wherein said goggles are swim goggles.

3. The goggles of claim 1, wherein said nosepiece is an elastomeric material.

4. The goggles of claim 1 wherein each of said end rings is flexible, resilient and of high tensile strength.

5. The goggles of claim 4 wherein said lug passageway has a width less than that of said end ring, so that said end ring must be compressed in width for passage through said lug passageway.

6. The goggles of claim 4 wherein said lug passageway has a dimension less than that of said end ring such that said end ring must be compressed in one dimension for passage through said lug passageway.

7. The goggles of claim 1 wherein a free end of said pin is tilted rearwardly away from said lug, whereby said respective one end ring is locked onto said pin while a force in the forward direction is applied to the respective one end ring.

8. The goggles of claim 1 wherein said pin extends inwardly towards the bridgepiece at least as far as said lug passageway.

9. The goggles of claim 8 wherein said pin is spaced rearwardly of said lug a distance sufficient to enable the passage therebetween of said respective one end ring.

10. The goggles of claim 1 characterized by the absence of cushioning on the rear of said eyepieces.

11. In goggles comprising:
   (A) a pair of eyepieces;
   (B) an elongate nosepiece connecting said pair of eyepieces to form an assembly; and
   (C) means for securing said assembly on a wearer's head, including an elastic band which, in conjunction with said pair of eyepieces and said nosepiece, encircles the wearer's head;
   the improvement wherein:
   (i) said nosepiece has a flexible and resilient bridgepiece adapted to pass over the bridge of the wearer's nose and, at each end of said bridgepiece, an end ring defining an aperture, each of said end rings being flexible and resilient; and
   (ii) each of said eyepieces is rigid and defines a lug extending inwardly towards said bridgepiece and a pin disposed rearwardly of said lug and extending inwardly, said lug defining a passageway therethrough for a respective one of said end rings, said lug passageway having a dimension less than that of said end ring, so that said end ring must be compressed in one dimension for passage through said lug passageway, and said pin being configured and dimensioned to enter and engage the aperture of said respective one end ring, a free end of said pin being tilted rearwardly away from said lug and extending inwardly towards said bridgepiece at least as far as said lug passageway, whereby said respective one end ring is locked onto said pin while a force in the forward direction is applied to said respective one end ring, said pin and said lug being spaced apart a distance sufficient to enable the passage therebetween of said respective one end ring and cooperatively precluding accidental disengagement of said end ring aperture and said pin, whereby said nosepiece and said eyepieces are releasably locked together to form the assembly.

12. A method of assembling goggles having a pair of eyepieces, an elongate nosepiece connecting the pair of eyepieces to form an assembly, and means for securing the assembly on a wearer's head, comprising the steps of:
   (A) providing (i) a pair of rigid eyepieces, each eyepiece having a passageway-defining lug extending inwardly in the direction of the nosepiece and a pin disposed rearwardly of the lug, (ii) a nosepiece having a flexible and resilient bridgepiece portion adapted to pass over the bridge of the wearer's nose and at each end thereof an end ring defining an aperture, and (iii) means for securing an assembly of the eyepieces and nosepiece on a wearer's head;
   (B) inserting each end ring through the passageway defined by a respective lug and then engaging the pin in the aperture of the end ring; and
   (C) applying the securing means to the outer end of each eyepiece.

13. The method of claim 12 wherein each of the end rings is flexible and resilient, and each of the lug passageways has a dimension less than that of the end ring, the method including the step of compressing the end ring in that dimension for insertion through the lug passageway.

14. In goggles including a pair of eyepieces and an elongated nosepiece for connecting said eyepieces, the improvement comprising said nosepiece being flexible and including integral female attachment members at the opposite ends thereof, and each of said eyepieces including at the inner side thereof an integral male member releasably receiving and engaging the adjacent female member, the corresponding engaged male and female members being oriented relative to each other such that the force normally exerted thereon by said nosepiece is in a direction to preclude inadvertent disengagement.

15. The goggles of claim 14 additionally including guide means formed on each of said eyepieces and positioned in relation to said male members to engage an end of said nosepiece and orient the same for attachment of said female member to said male member.

16. The goggles of claim 15 wherein said guide means is a slot formed in said eyepiece having its major axis at an obtuse angle to the major axis of said male member.

17. The goggles of claim 15 wherein said female members must be compressed in at least one dimension to pass through said guide means.

18. The goggles of claim 14 wherein said male and female members are configured and dimensioned to frictionally engage.

19. The goggles of claim 14 wherein said nose piece is fabricated of a resilient, flexible elastomer.

* * * * *